United States Patent
Kandori et al.

(10) Patent No.: US 7,400,984 B2
(45) Date of Patent: Jul. 15, 2008

(54) BIOMAGNETIC MEASUREMENT APPARATUS

(75) Inventors: Akihiko Kandori, Kokubunji (JP); Keiji Tsukada, Okayama (JP); Tsuyoshi Miyashita, Fuchu (JP); Kuniomi Ogata, Hachioji (JP)

(73) Assignee: Hitachi High-Technologies, Corp., Tokyo (JP)

( * ) Notice: Subject to any disclaimer, the term of this patent is extended or adjusted under 35 U.S.C. 154(b) by 788 days.

(21) Appl. No.: 10/822,715

(22) Filed: Apr. 13, 2004

(65) Prior Publication Data
US 2004/0210127 A1 Oct. 21, 2004

(30) Foreign Application Priority Data
Apr. 18, 2003 (JP) ............................. 2003-114508

(51) Int. Cl.
*G06F 19/00* (2006.01)
*A61B 5/05* (2006.01)

(52) U.S. Cl. ........................................ 702/38; 600/409

(58) Field of Classification Search ................... 702/19, 702/38, 66, 67; 600/481, 508, 509, 513
See application file for complete search history.

(56) References Cited

U.S. PATENT DOCUMENTS 6,230,037 B1 * 5/2001 Tsukada et al. ............. 600/409
6,473,650 B1 * 10/2002 Larsson et al. ................ 607/28
7,123,952 B2 * 10/2006 Nakai et al. .................. 600/509

FOREIGN PATENT DOCUMENTS

| JP | 10-248821 | | 9/1998 |
| JP | 10-305019 | | 11/1998 |
| JP | 11-151221 | | 6/1999 |
| JP | 2002-028143 | * | 1/2002 |

* cited by examiner

*Primary Examiner*—Michael P Nghiem
(74) *Attorney, Agent, or Firm*—Mattingly, Stanger, Malur & Brundidge, PC

(57) ABSTRACT

A biomagnetic measurement technique which can obtain a potential waveform corresponding to a ventricular muscle cell action potential in a non-invasive manner. The biomagnetic measurement apparatus including an operating circuit for magnetometer. The output data of the operating circuit for the magnetometer is collected and a current vector at time t is calculated. Further, an absolute value Ixy of the current vector, a potential waveform V (t) in time corresponding to depolarization of a heart from the absolute value of the current vector, and a potential waveform V (t) in a refractory period of the heart to a period corresponding to repolarization from the absolute value of the current vector are calculated.

13 Claims, 10 Drawing Sheets

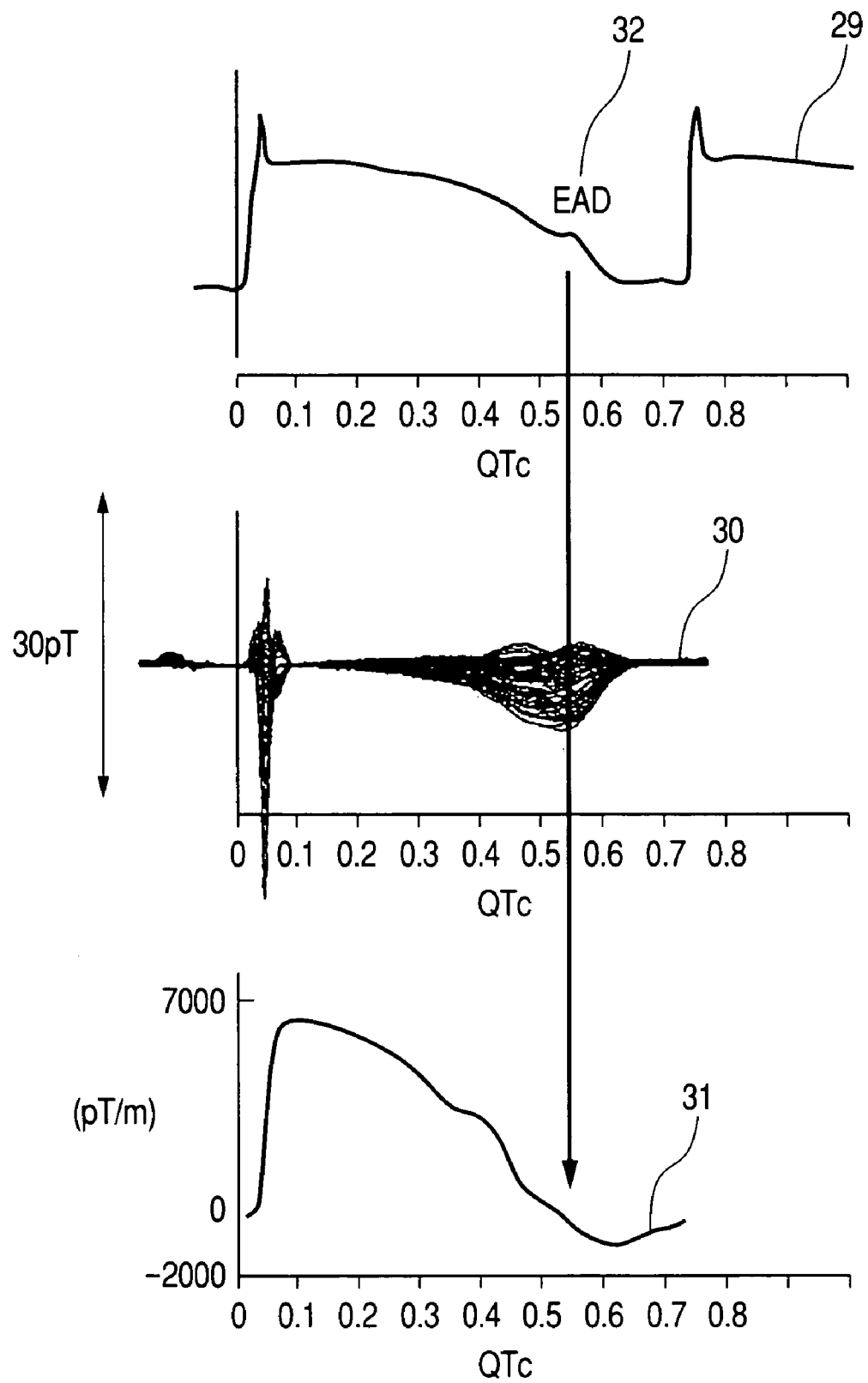

BIOMAGNETIC MEASUREMENT APPARATUS

CLAIM OF PRIORITY

The present invention claims priority from Japanese application JP 2003-114508 filed on Apr. 18, 2003, the content of which is hereby incorporated by reference on to this application.

BACKGROUND OF THE INVENTION

The present invention relates to a biomagnetic measurement technique detecting a very weak magnetic field such as a magnetocardiogram and a magnetoencephalogram using an SQUID (superconducting quantum interference device) magnetometer as a superconducting device.

An action potential occurs by excitation of a ventricular muscle to produce a very weak electric current in the ventricular muscle in appearance. Along with the electric current, a very weak magnetic field is produced outside a living body. The very weak magnetic field from a heart (hereinafter, abbreviated as a "magnetocardiogram") is measured using a highly sensitive magnetic sensor called a superconducting quantum interference device (SQUID). The magnetocardiogram is less affected by the conductivity of a living body, which is hard to be subject to waveform distortion. From the measurement result of the magnetocardiogram, an attempt to image an electric current activity on the surface of a ventricular muscle has been made.

In the attempt to image an electric current activity, there is proposed a method for calculating $Ix=dBz/dy$ and $Iy=-dBz/dx$ from a magnetic field (Bz) of a vertical (z) element to the surface of a living body to reconstruct a distribution of imaginary current vectors $I=(Ix, Iy)$ (for example, see Japanese Patent Application Laid-Open No. 10-248821).

As an ischemic area identification method, there is proposed a method for calculating the total of absolute values of the imaginary current vectors I in a predetermined period (for example, see Japanese Patent Application Laid-Open Nos. 10-305019 and 11-151221). An ischemic area is estimated by mapping of the total value in the predetermined period.

As an invasive method for directly measuring a ventricular muscle action potential, there is catheter mapping. The catheter mapping is a method for directly contacting a catheter having at its edge a plurality of potential measurement electrodes with the inner surface of a heart to measure a ventricular muscle action potential.

SUMMARY OF THE INVENTION

In the above prior art, the amount of electric current can be calculated by a distribution of current vectors and the total of absolute values of the current vectors in a predetermined time. No waveforms corresponding to a ventricular muscle action potential can be measured. The catheter mapping in the prior art is a method for inserting a catheter into a body under X-ray radiation, which is an examination putting a large load on patients.

An object of the present invention is to provide a biomagnetic measurement technique which can obtain a potential waveform corresponding to a ventricular muscle cell action potential in a non-invasive manner.

To achieve the above object, in a biomagnetic measurement apparatus of the present invention, when a plane in parallel with a plane contacted with the surface of a living body is xy plane and an axis vertical to the xy plane is z, a magnetic field produced from a heart is detected by a plurality of magnetometers including superconducting quantum interference devices. The superconducting quantum interference devices are driven by an operating circuit for magnetometer. Output data (signal data) of the operating circuit for magnetometer are collected by a data collection device. An operation processor executes operation processing of the collected output data (signal data). The result of the operation processing is displayed on a display device.

$Ix=dBz/dy$ and $Iy=-dBz/dx$ are calculated from a detected magnetic field $(Bz (x, y))$ of a vertical (z) element to the surface of a living body to calculate imaginary current vector $I=(Ix, Iy)$. An absolute value of the current vector is calculated by using $Ixy(t)=\sqrt{\{(Ix(t))^2+(Iy(t))^2\}}$.

When a potential waveform at start time $t_0$ of depolarization of the heart (a period in which QRS wave appears) is V $(t_0)=0$ or Ixy $(t_0)=0$ and end time of repolarization is $t_n$, a potential waveform at time $t_i$ (i=0, 1, ..., m) in a period from the $t_0$ to end time $t_m$ of depolarization of the heart is calculated by using $V(t_i)=V(t_{i-1})+Ixy(t_i)$. The value of potential waveform $V(t_m)$ at the end time $t_m$ of depolarization is $V_m$.

A potential waveform at the start time $t_{m+1}$ of repolarization of the heart (a period in which ST-T wave appears) is calculated by using $V(t_{m+1})=V_m-Ixy(t_{m+1})$. A potential waveform at time $t_i$ (i=m+2, m+3, ..., n) in a period from the time $t_{m+2}$ in a period of repolarization to the end time $t_n$ of repolarization is calculated by using $V(t_i)=V(t_{i-1})-Ixy(t_i)$.

The method for obtaining the imaginary current vector I is not limited to calculation of $Ix=dBz/dy$ and $Iy=-dBz/dx$. A current vector calculated by a solving method of inverse problem using a lead field matrix and a current vector using a minimum norm method may be used.

More specifically, the operation processor executes the following first to third operation processing.

In the first operation processing, when $t=t_i$ (i=0, 1, ..., m) is a period corresponding to depolarization of the heart of the living body and $t=t_i$ (i=m+1, m+2, ..., n) is a period corresponding to repolarization of the heart of the living body, from the element Bz in the z direction at time t at the measurement point (x, y), a current vector (Ix (t), Iy (t)) at time t and an absolute value of the current vector (Ixy (t)=$\sqrt{\{(Ix(t))^2+I(t))^2\}}$) is calculated at time $t_i$ (i=0, 1, ..., n).

In the second operation processing, when the lower limit of addition $\Sigma$ is i=0 and the upper limit of addition $\Sigma$ is i=0, 1, ..., m, a potential waveform at time $t=t_i$ (i=0, 1, ..., m) in a period corresponding to depolarization of the heart of the living body is calculated by using $V(t_i)=\Sigma Ixy(t_i)$.

In the third operation processing, when the value of the potential waveform $V(t_m)$ at the end of a period corresponding to depolarization of the heart of the living body is $V_m$, the lower limit of addition $\Sigma$ is i=m+1, and the upper limit of addition Z is i=m+1, m+2, ..., n, a potential waveform at time $t=t_i$ (i=m+1, m+2, ..., n) in a period corresponding to repolarization of the heart of the living body is calculated by using $V(t_i)=V_m-\Sigma Ixy(t_i)$.

The potential waveform V (x, y, t) at time $t=t_i$ (i=0, 1, ..., n) at the measurement point (x, y), which is obtained in the second and third operation processing, is displayed on the display device. The operation processor calculates the potential waveforms V (x, y, t) at a plurality of measurement points (x, y) The equipotential diagram connecting the equipotential points of the potential waveforms V (x, y, t) calculated at the plurality of measurement points (x, y) is displayed by contour map. The waveform of the measured magnetic field and the potential waveform V (x, y, t) are displayed on the display device.

The biomagnetic measurement apparatus and the data processing method of the present invention can obtain an action potential waveform corresponding to each area of a heart. Information on an abnormal ventricular muscle action potential such as long QT syndrome can be obtained in a non-invasive manner.

BRIEF DESCRIPTION OF THE DRAWINGS

FIG. 10 is a diagram showing comparison of a ventricular muscle potential measurement result (the top figure) by a catheter examination measured in the right ventricular wall of a patient having Type I long QT syndrome, an overlapped figure (the middle figure) of the magnetocardiogram waveforms, and the calculated action potential waveform (the bottom figure) according to the embodiment of the present invention.

DETAILED DESCRIPTION OF THE PREFERRED EMBODIMENTS

Figure 1:
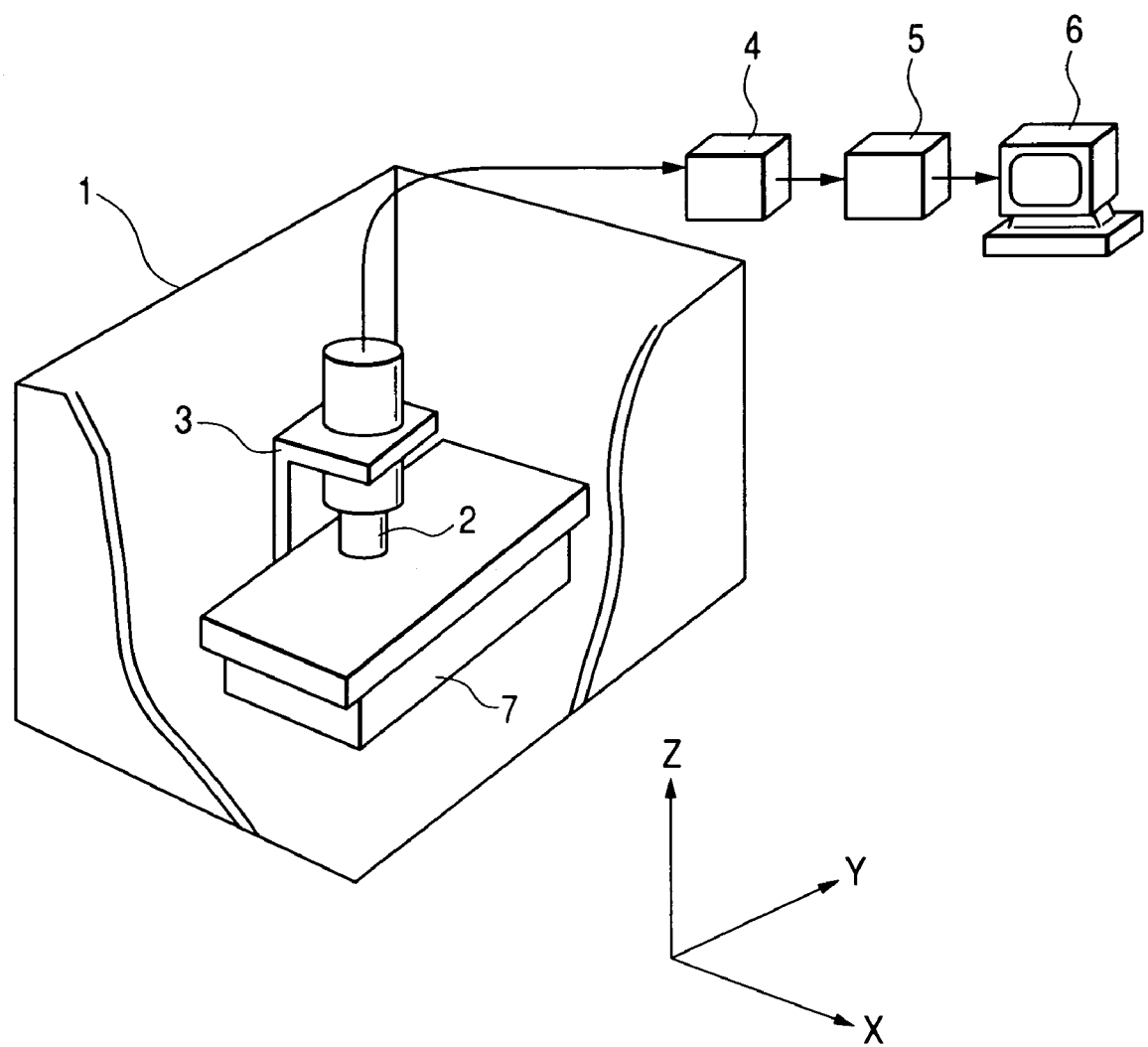
FIG. 1 is a diagram showing the configuration example of a biomagnetic measurement apparatus of an embodiment of the present invention.

A biomagnetic measurement apparatus of an embodiment of the present invention in which when a plane in parallel with a plane contacted with the surface of a chest is xy plane and an axis vertical to the (x, y) plane is z, current vectors from magnetic fields produced from a heart and absolute values of the current vectors are calculated at a plurality of measurement points (x, y), wherein potential waveforms at the plurality of measurement points (x, y) are calculated based on current vectors in a period from start time of depolarization of the heart to end time of depolarization of the heart and absolute values of the current vectors in a period from the end of depolarization of the heart to end time of repolarization of the heart, thereby detecting information on early afterdepolarization of the heart.

In a period from start time of depolarization of the heart to end time of depolarization of the heart, absolute values of the current vectors are added to calculate a potential waveform.

In a period from the end of depolarization of the heart to end time of repolarization of the heart, the absolute values of the current vectors are subtracted from the value of the potential waveform at the end of depolarization of the heart to calculate potential waveforms at the plurality of measurement points (x, y).

More specifically, when start time of depolarization of the heart is $t_0$, end time of depolarization of the heart is $t_m$, end time of repolarization of the heart is $t_n$, an absolute value of a current vector at time $t_i$ is Ixy ($t_i$), and a potential waveform at the time to is V ($t_0$)=0, a potential waveform at time $t_i$ in a period from the time $t_0$ to time $t_m$ is calculated by using V ($t_i$)=V ($t_{i-1}$)+Ixy ($t_i$). The value of potential waveform V ($t_m$) at the time $t_m$ is $V_m$, and a potential waveform at the time $t_{m+1}$ is calculated by using V ($t_{m+1}$)=$V_m$-Ixy ($t_{m+1}$). A potential waveform at time $t_i$ in a period from time $t_{m+2}$ to time $t_n$ is calculated by using V ($t_i$)=V ($t_{i-1}$)-Ixy ($t_i$). The potential waveforms V ($t_i$) are calculated at the respective measurement points (x, y). Information on early afterdepolarization can be detected from the potential waveforms V (x, y, t) calculated at the plurality of measurement points (x, y). The thus-calculated potential waveform V (x, y, $t_i$) corresponding to each area of the heart is displayed on the display device.

A data processing method in the biomagnetic measurement apparatus of the present invention having a plurality of detection coils detecting, when a plane in parallel with a plane contacted with a living body is xy plane and an axis vertical to the (x, y) plane is z, element Bz in z direction of a magnetic field produced from the living body, and a data collection device collecting detected signal data of the element Bz in the z direction, which is executed after collecting the signal data, wherein in a period from start time of depolarization of the heart to end time of depolarization of the heart, absolute values of current vectors are added to calculate a potential waveform, and in a period from the end of depolarization of the heart to end time of repolarization of the heart, the absolute values of the current vectors are subtracted from the value of the potential waveform at the end of depolarization of the heart to calculate potential waveforms at a plurality of measurement points (x, y).

More specifically, when start time of depolarization of the heart is $t_0$, end time of depolarization of the heart is $t_m$, end time of repolarization of the heart is $t_n$, an absolute value of a current vector at time $t_i$ is Ixy ($t_i$) (i=1, 2, . . . , n), and a potential waveform at the time $t_0$ is V ($t_0$)=0, a potential waveform at time $t_i$ in a period from the time $t_0$ to the time $t_m$ is calculated by using V ($t_i$)=V ($t_{i-1}$)+Ixy ($t_i$). The value of potential waveform V ($t_m$) at the time $t_m$ is $V_m$, and a potential waveform at the time $t_{m+1}$ is calculated by using V ($t_{m+1}$)= $V_m$-Ixy ($t_{m+1}$). A potential waveform at time $t_i$ in a period from the time $t_{m+2}$ to the time $t_n$ is calculated by using V ($t_i$)=V ($t_{i-1}$)-Ixy ($t_i$) The potential waveforms V ($t_i$) are calculated at the respective measurement points (x, y).

An embodiment of the present invention will be described below in detail based on the drawings.

FIG. 1 is a diagram showing the configuration example of a biomagnetic measurement apparatus according to an embodiment of the present invention. In a magnetically shielded room 1, there are arranged a bed 7 on which a living body is placed, a cryostat 2 storing a refrigerant (liquid helium or liquid nitrogen) for holding SQUID sensors in a superconducting state, and a gantry 3 for fixing the position of the cryostat 2. The SQUID sensors are operated as magnetometers by a driving circuit 4 arranged outside the magnetic shield room 1. The outputs of the magnetometers pass through an amp filter unit 5 to be converted to digital data by an A/D converter circuit incorporated in a computer 6, and are then stored in the computer 6.

Figure 2:
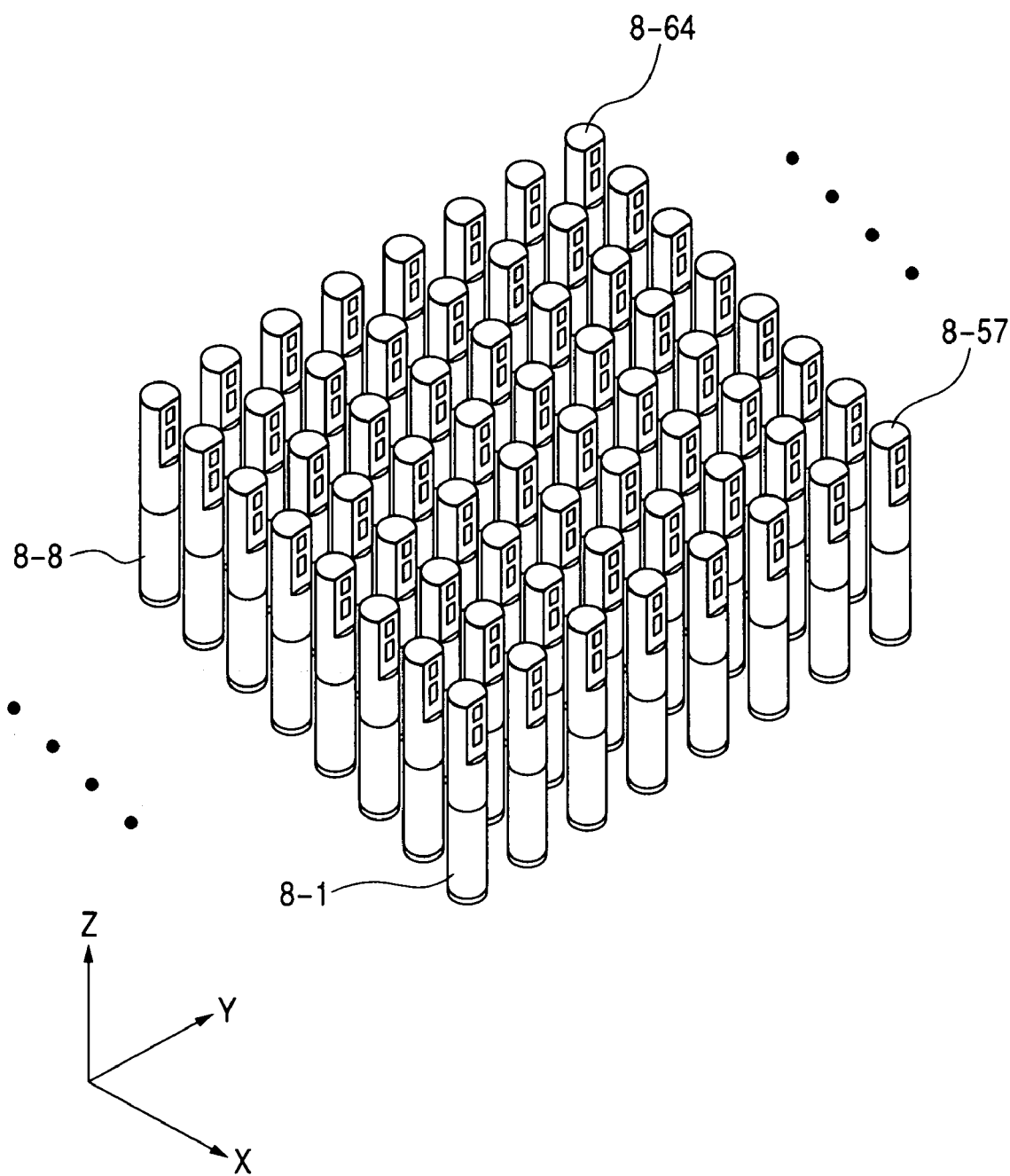
FIG. 2 is a diagram showing an example of an array of detection coils arranged in the cryostat of FIG. 1.

FIG. 2 is a diagram showing an example of an array of detection coils 8 arranged in the cryostat 2 of FIG. 1. The detection coils 8 are integrated with the SQUID sensors. In the example shown in FIG. 2, the detection coils integrated with the SQUID sensors 8-1 to 8-64 are arranged in an 8×8 matrix. The arrangement in a matrix facilitates calculation of a current vector of the present invention (which will be described later in detail). As the current vector calculation method, there are a minimum norm method and a method for calculating a lead field inverse matrix. The detecti8on coils are not necessarily arranged as shown in FIG. 2.

Figure 3:
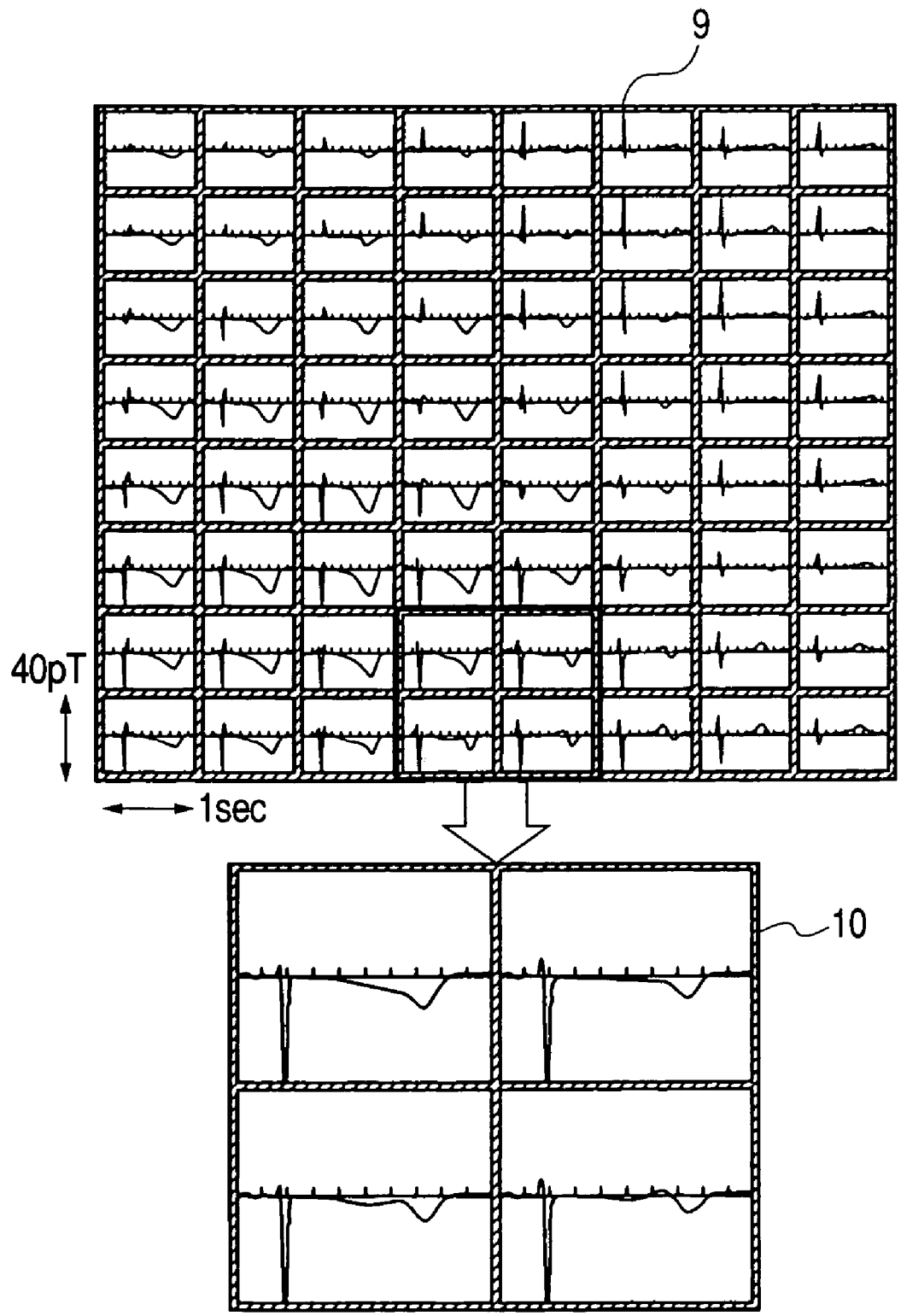
FIG. 3 is a diagram showing an example of magnetocardiograms measured by the biomagnetic measurement apparatus of FIG. 1.

FIG. 3 is a diagram showing an example of a magnetic field waveform (hereinafter, called a "magnetocardiogram waveform") measured in the heart of a patient having Type I long QT syndrome by the biomagnetic measurement apparatus of FIG. 1. The top figure of FIG. 3 shows a grid map 9 showing magnetic field waveforms corresponding to the respective positions (channels) of the detection coils 8-1 to 8-64 shown in FIG. 2. The bottom figure of FIG. 3 shows an enlarged FIG. 10 of the grid map in four positions in which characteristic magnetic field waveforms appear. From the enlarged FIG. 10, in the lower parts of the detection coils in four positions (channels), it is found that two-layer (notch type) characteristic waveforms appear. In FIG. 3, the double-headed arrow line on the horizontal axis indicates a time width of 1 sec, and the double-headed arrow line on the vertical axis indicates 40 pT.

Figure 4:
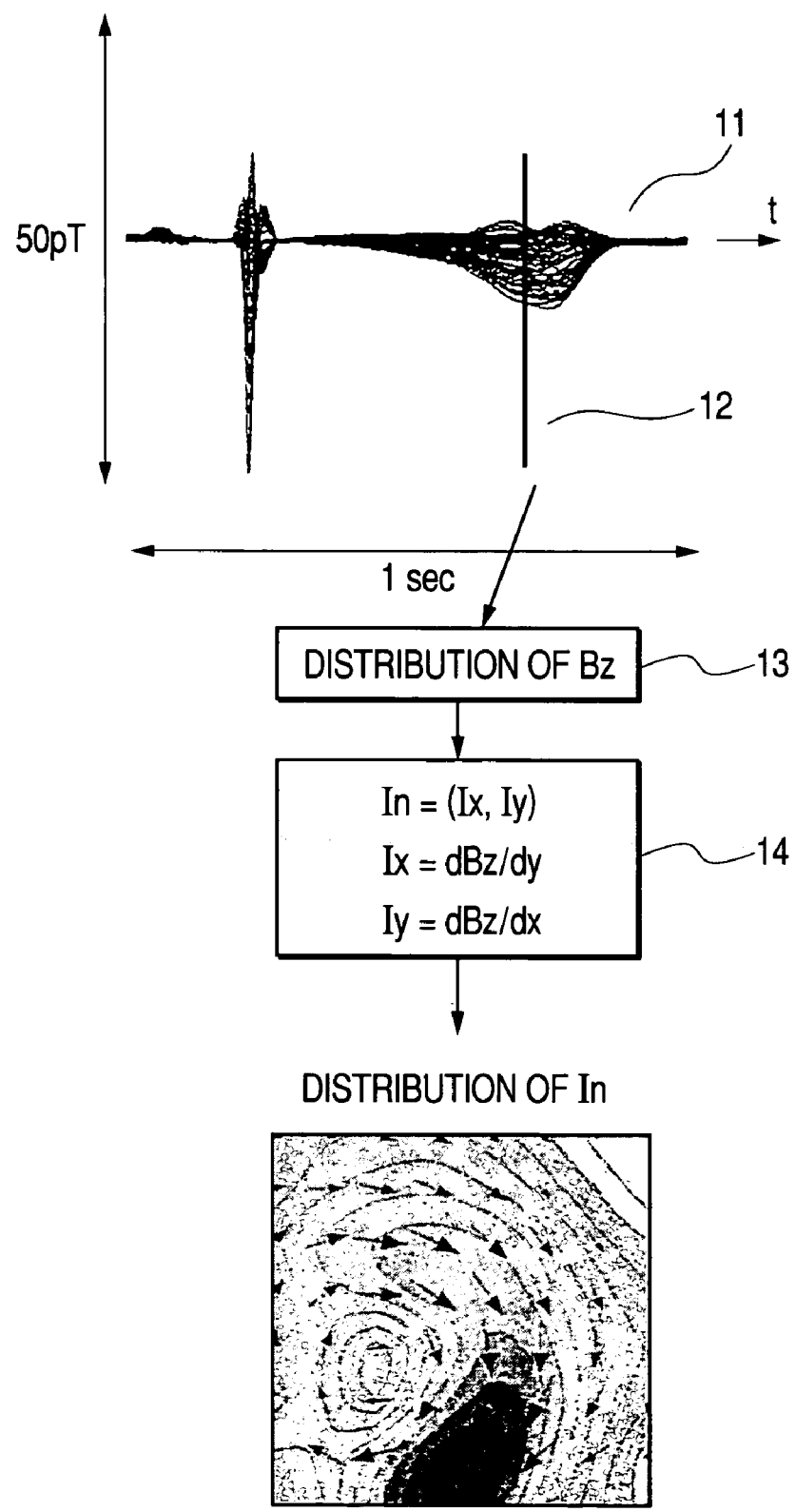
FIG. 4 is a diagram showing a current vector calculation method of the present invention.

FIG. 4 is a diagram showing a process creating a current vector from the z element (Bz (x, y)) of a magnetic field used in the embodiment of the present invention. The top figure of FIG. 4 shows an overlapped waveform 11 of magnetic field waveforms in which the magnetocardiogram waveforms (the grid map 9) of 64 channels shown in FIG. 3 are overlapped with each other on one trace to be displayed.

Using a distribution 13 of Bz (x, y) at an observation time 12 of a distribution 15 of current vectors In (x, y), calculation 14 of the current vector In is performed by Ix=dBz/dy and Iy=−dBz/dx. This can obtain the distribution 15 of current vectors In (x, y) showing directions and magnitudes by straight lines with arrows. The distribution 15 of current vectors In shows actual data about a patient having Type I long QT syndrome. It is found that abnormal current (the black part in the figure) is produced in the lower part of the measured plane of the magnetocardiogram. In FIG. 4, the double-headed arrow line on the horizontal axis indicates a time width of 1 sec, and the double-headed arrow line on the vertical axis indicates 50 pT.

As the current vector calculation method, the minimum norm method and the method for calculating a lead field inverse matrix may be used.

Figure 5:
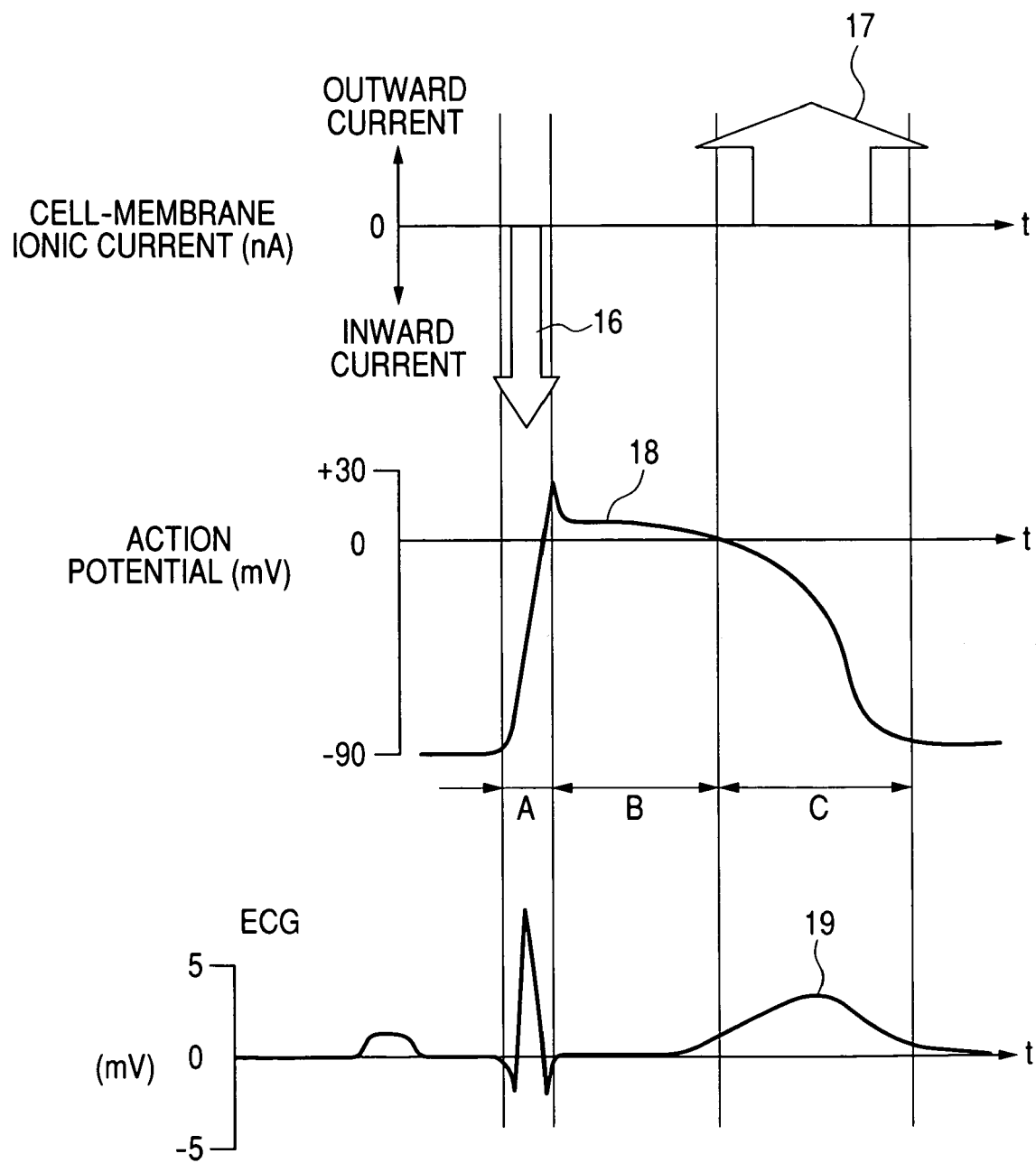
FIG. 5 is a diagram showing the relation between a cell-membrane ionic current, a ventricular muscle action potential and an ECG according to the embodiment of the present invention.

FIG. 5 is a diagram showing the relation between a cell-membrane ionic current, a ventricular muscle action potential and an ECG according to the embodiment of the present invention. The distributions of ion concentrations are different inside and outside the ventricular muscle cell. When the permeability of a cell-membrane ion is selectively advanced, the ion is flowed in or out of the cell according to the electro-chemical potential gradient. The ion flowed in and out of the cell membrane can be considered as an electric current, which is called a cell-membrane ionic current. The entrance of the cell-membrane ionic current is called an ion channel. FIG. 5 shows a representative cell-membrane ionic current.

In depolarization period A, an inward current (an electric current flowing from outside the cell to inside the cell) 16 having a large amount of electric current is flowed inside the cell in a short time. As the representative inward current 16, there is Na+electric current (INa). After that, the ventricular muscle is brought to plateau phase (refractory period) B during which period there is no significant cell-membrane ionic current movement. Finally, it is brought to repolarization period C so that an outward current (an electric current flowing out from inside the cell to outside the cell) 17 is slowly flowed out from inside the cell. As the representative cell-membrane ionic current of the outward current 17, there is K+electric current (IK). It is found that a large number of ions are involved in the inward current 16 and the outward current 17. FIG. 5 is a schematic diagram showing the cell-membrane ionic current very simply.

A ventricular muscle action potential 18 is formed by the cell-membrane ionic currents (16, 17) flowed out from outside the cell or to inside the cell. The ventricular muscle action potential 18 is a waveform performing synthesis in the present invention.

The bottom figure of FIG. 5 shows an ECG waveform 19 finally measured as the potential of the surface of the living body by the total electric activity of the ventricular muscle action potential 18. It is considered that the ECG waveform is formed by the differential potential between the action potential of the endocardium and the action potential of the epicardium of a ventricular muscle cell or the differential potential (electrical propagation) between the action potentials of adjacent ventricular muscle cells. As a result, in the ECG waveform 19, QRS waveform appears in the depolarization period A and T wave appears in the repolarization period C.

Figure 6:
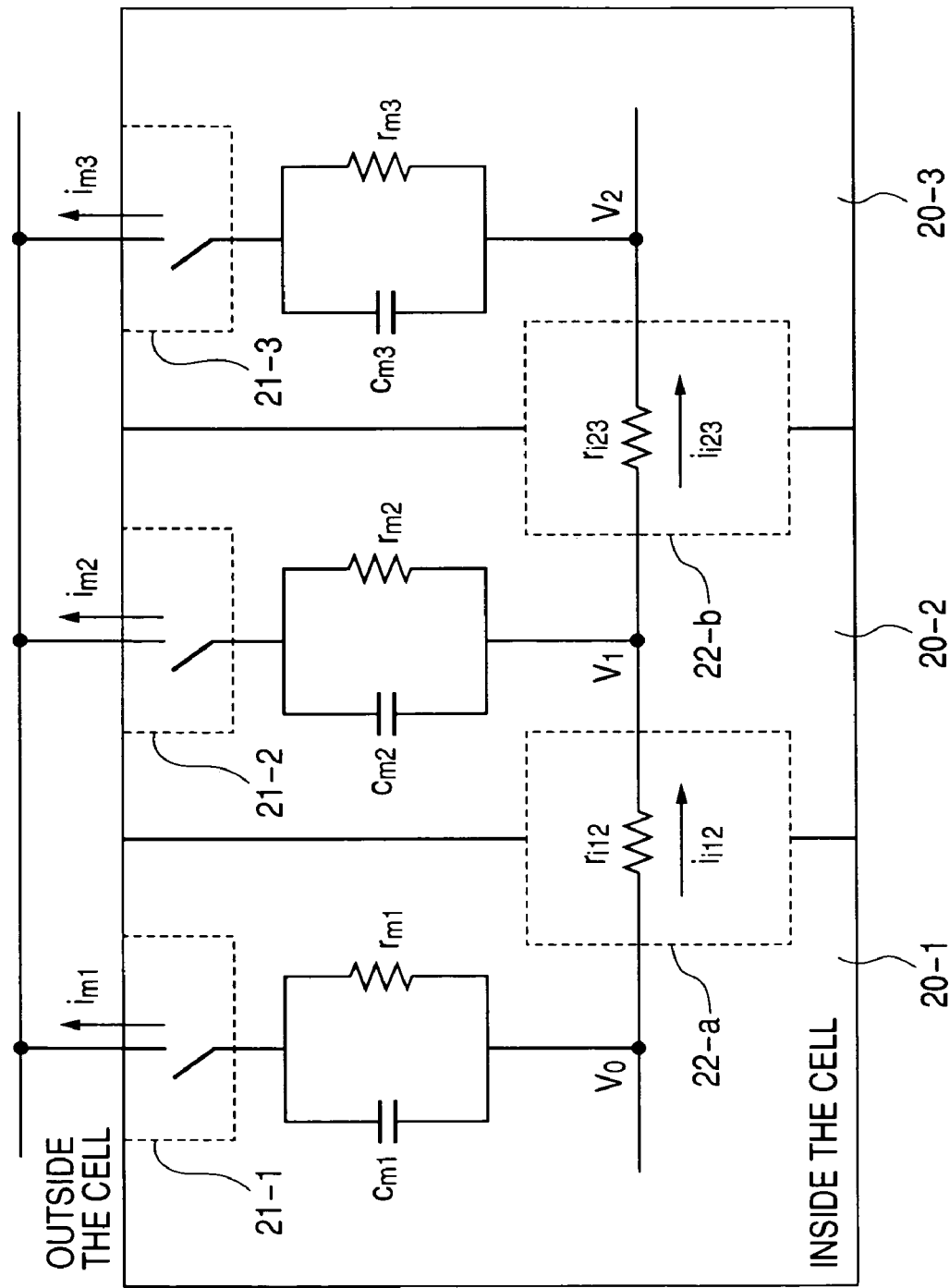
FIG. 6 is an equivalent circuit diagram of assistance in explaining a mechanism about electrical propagation of adjacent ventricular muscle cells according to the embodiment of the present invention.

FIG. 6 is an equivalent circuit diagram of assistance in explaining a mechanism about electrical propagation of adjacent ventricular muscle cells according to the embodiment of the present invention.

FIG. 6 shows three-dimensional ventricular muscle tissue as a two-dimensional propagation model with three ventricular muscle cells 20-1, 20-2 and 20-3. Only electrical propagation at depolarization will be described here. When an electric signal transmitted from the stimulation transmission system of the heart in the left direction is transmitted to $V_0$ and $V_0$ in the ventricular muscle cell 20-1 exceeds the threshold value (about −60 to −70 mV), the switch of an ion channel 21-1 is opened to start flowing cell-membrane ionic current $i_{m1}$ as the inward current via a parallel circuit having resistance $r_{m1}$ and capacitance $C_{m1}$. The flowing of the cell-membrane ionic current $i_{m1}$ produces an action potential specific to the ventricular muscle cell 20-1 in the $V_0$.

Subsequently, electric current $i_{i12}$ is flowed via junction resistance $r_{i12}$ to a gap junction part 22-a of the ventricular muscle cells to produce an action potential in V1 in the ventricular muscle cell 20-2. As in the ventricular muscle cell 20-1, when the V1 exceeds the threshold value (about −60 to −70 mV), the switch of an ion channel 21-2 is opened to start flowing cell-membrane ionic current $i_{m2}$ as the inward current via a parallel circuit having resistance $r_{m2}$ and capacitance $C_{m2}$. The cell-membrane ionic current $i_{m2}$ produces an action potential specific to the ventricular muscle cell 20-2 in the $V_1$.

Subsequently, electric current $i_{i23}$ is flowed via junction resistance $r_{i23}$ to a gap junction part 22-b of the ventricular muscle cells to produce an action potential in $V_2$ in the ventricular muscle cell 20-3. The excitation is propagated to the adjacent ventricular muscle cells. It is supposed here that signals trapped in the magnetocardiogram are the electric currents $i_{i12}$ and $i_{i23}$ considered to be the propagation signals.

Under the supposition, the electric currents in the ventricular muscle at a certain time are considered to be $i_{i12}=(V_1-V_0)/r_{i12}$ and $i_{i23}=(V_2-V_1)/r_{i23}$, which reflect the potential difference between the cells. To calculate an action potential of each ventricular muscle cell, an action potential at time at which cell excitation does not occur must be zero to calculate the total amount of electric current corresponding to ventricular muscle electrical excitation sequentially produced. It is considered that a potential corresponding to an action potential can be calculated by the total amount of electric current. In the above description, due to calculation at depolarization, the total amount of electric current is considered as the action potential calculation method. At repolarization for the outward current (in the direction opposite the inward current at depolarization), there is performed a method for subtracting from the total of electric currents (which will be described in detail in FIGS. 7 and 8).

Figure 7:
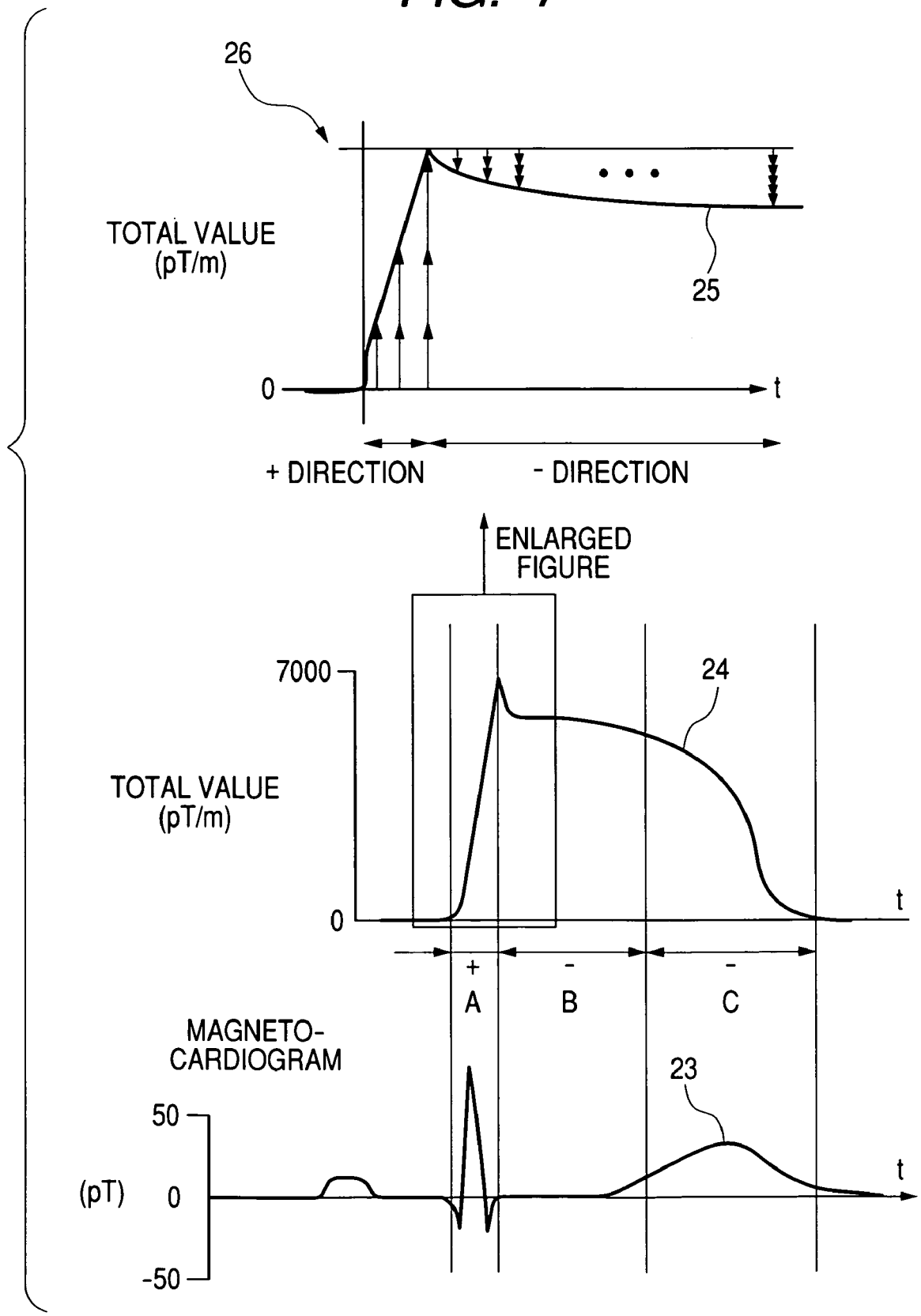
FIG. 7 is a diagram schematically showing an example of a method for calculating a ventricular muscle action potential waveform according to the embodiment of the present invention.

FIG. 7 is a diagram schematically showing a method for obtaining a ventricular muscle action potential waveform according to the embodiment of the present invention. FIG. 7 shows a schematic diagram of the action potential calculation described in FIG. 6. FIG. 6 assumes that a current vector is calculated in a certain magnetocardiogram measurement position (channel). In the depolarization period (QRS waveform) A of a magnetocardiogram waveform 23, as shown in an enlarged FIG. 25 of the obtained action-potential waveform, absolute values of current vectors are added. The absolute values of the current vectors are added in the + direction to obtain a total value.

In time from the start of the refractory period B to the end of the repolarization period C, the absolute values of the current vectors are subtracted from the largest value 26 at the end of the depolarization period (QRS waveform) A. The absolute values of the current vectors are subtracted (or added in the − direction). As a result, an action potential waveform 24 is obtained.

Figure 8:
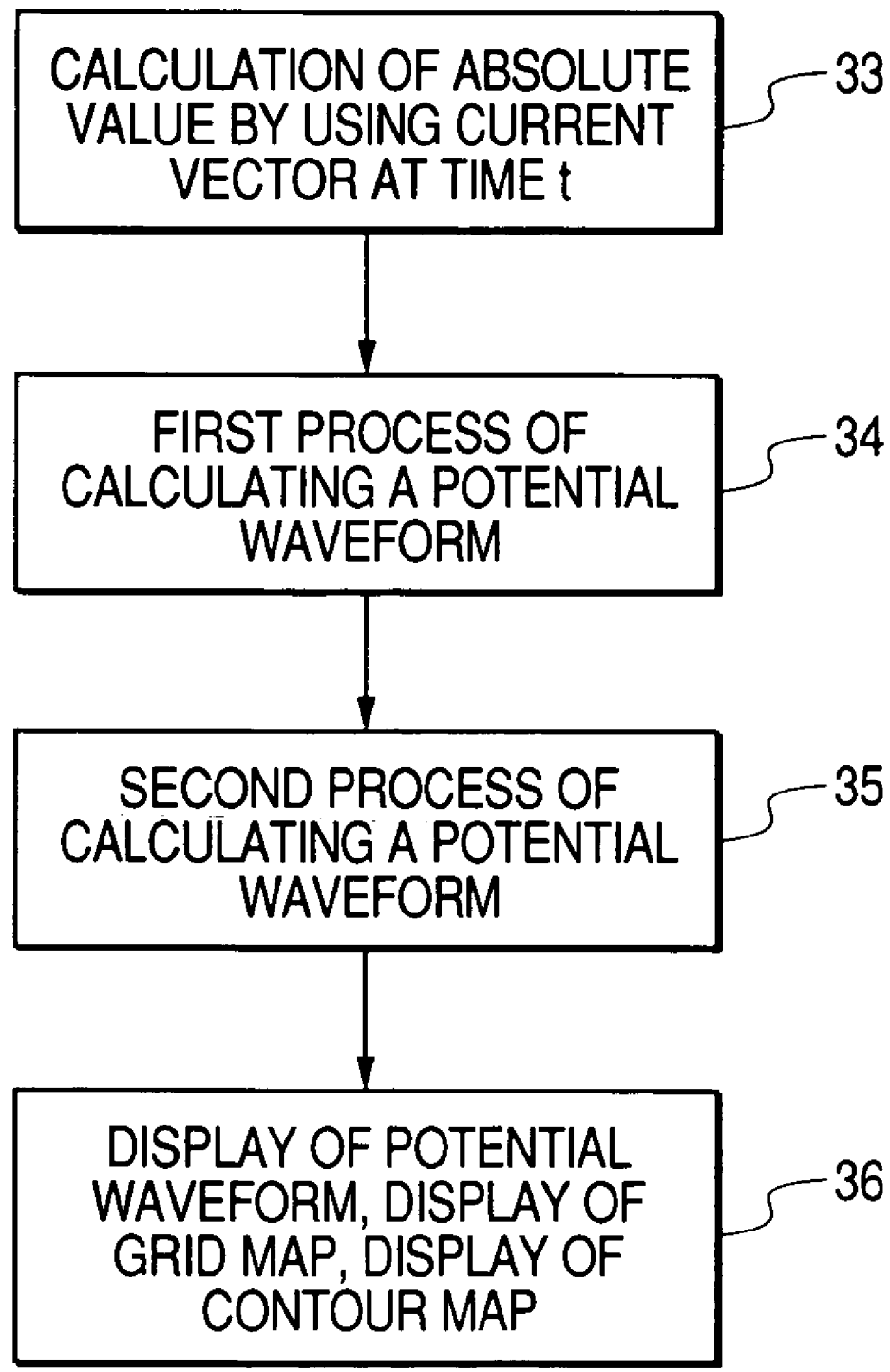
FIG. 8 is a diagram of assistance in explaining an example of calculation processes calculating a ventricular muscle action potential waveform according to the embodiment of the present invention.

FIG. 8 is a diagram of assistance in explaining calculation processes obtaining a ventricular muscle action potential waveform according to the embodiment of the present invention.

In the following description, $t=t_i$ ($i=0, 1, \ldots, m$) is a period corresponding to depolarization of the heart of the living body and $t=t_i$ ($i=m+1, m+2, \ldots, n$) is a period including the refractory period B to the end of repolarization of the heart.

From a magnetic field measured at time $t=t_i$ ($i=0, 1, \ldots, n$), a current vector ($Ix(t), Iy(t)$) and an absolute value of the current vector $(Ixy(t) = \sqrt{(Ix(t))^2 + (Iy(t))^2}$ are calculated (a process 33 calculating an absolute value of a current vector). In a period of depolarization of the heart, absolute values of current vectors are added. When the lower limit of addition $\Sigma$ is $i=0$ and the upper limit of addition $\Sigma$ is $i=0, 1, \ldots, m$, a potential waveform at time $t=t_i$ ($i=0, 1, \ldots, m$) in a period corresponding to depolarization of the heart is calculated by using $V(t_i) = \Sigma Ixy(t_i)$. Here, the junction resistance of the gap junction part is considered to be 1.

More specifically, $V(t_0)=Ixy(t_0)$; $V(t_1)=Ixy(t_0)+Ixy(t_1)$; $V(t_2)=Ixy(t_0)+Ixy(t_1)+Ixy(t_2)$; ...; $V(tr)=Ixy(t_0)+Ixy(t_1)+ \ldots +Ixy(t_m)=V_m$ are calculated (a first process 34 calculating potential waveform V). $V_m$ is the largest value 26 of the potential waveform at the end of the period corresponding to depolarization of the heart.

In a period from the start of the refractory period B to the end of the repolarization period C, the absolute values of the current vectors are subtracted from the largest value 26 at the end of the depolarization period (QRS waveform) A. When the lower limit of addition $\Sigma$ is $i=m+1$ and the upper limit of addition $\Sigma$ is $i=m+1, m+2, \ldots, n$, the absolute values of the current vectors are subtracted to calculate a potential waveform at time $t=t_i$ ($i=m+1, m+2, \ldots, n$) by using $V(t_i)=Vm-\Sigma Ixy(t_i)$.

More specifically, $V(t_{m+1})=V_{m-1}xy(t_{m+1})$; $V(t_{m+2}))=V_m-Ixy(t_{m+1})-Ixy(t_{m+2})$; ...; $V(t_n)=V_m-Ixy(t_{m+1})-Ixy(t_{m+2})-\ldots-Ixy(t_n)$ are calculated (a second process 35 calculating potential waveform V).

In the result of the second process 35, a display process 36 performs waveform display of the potential waveform V (the bottom figure of FIG. 9), grid map display (the top figure of FIG. 9), and contour map display of an equipotential diagram connecting the equipotential points of the potential waveform V. Data for diagnosis are provided as display easily understood by an examiner. Data about the contour map display are omitted.

Figure 9:
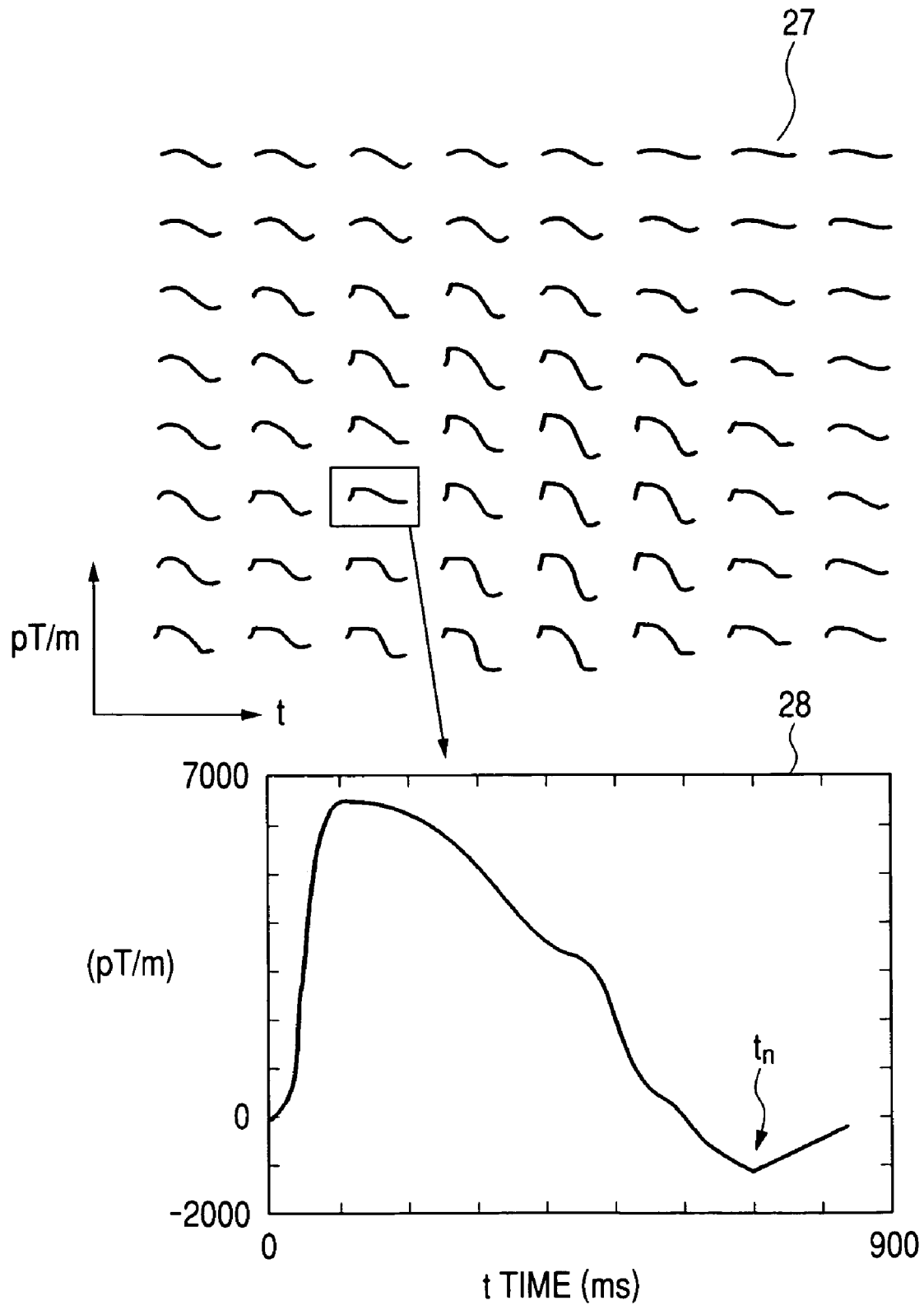
FIG. 9 is a diagram showing an example of ventricular muscle action potential waveforms calculated from the magnetocardiogram waveforms of FIG. 3.

FIG. 9 is a diagram showing ventricular muscle action potential waveforms obtained from the magnetocardiogram waveforms of FIG. 3. FIG. 9 displays action potential waveforms 27 about 64 channels calculated using actually measured data of the patient having Type I long QT syndrome shown in FIG. 3. In particular, the action potential waveform of the area in which the action potential waveform 27 shows a characteristic pattern is shown as an enlarged FIG. 28. The action potential waveform showing a characteristic pattern appears in an area almost corresponding to a right ventricle.

According to the embodiment of the present invention, FIG. 10 shows, on one trace at the same time, a ventricular muscle potential measurement result 29 of one channel by a catheter examination measured in the right ventricular wall of the same patient (having Type I long QT syndrome) with the measured magnetic field waveforms (magnetocardiogram waveforms) of FIG. 3, a magnetocardiogram waveform overlapped FIG. 30, and an obtained action potential waveform 31 (the potential waveform in the right ventricle shown in the enlarged figure of FIG. 9). Time on the horizontal axis is indicated by standardized QTc having RR interval of 1. One or more magnetocardiogram waveforms and one or more ventricular action potential waveforms are displayed on the same slide at the same time to easily understand the relation between the magnetocardiogram waveform and the ventricular action potential waveform.

When observing the ventricular muscle potential measurement result 29, a notch can be found in the calculated action potential waveform 31 at time at which early afterdepolarization (EAD) 32 occurs. The ventricular muscle potential measurement result 29 coincides well with the calculated action potential waveform 31. They are found to have been measured in the same right ventricle. The effectiveness of the ventricular muscle action potential waveform calculation method according to the embodiment of the present invention can be understood. The present invention can obtain information on an abnormal ventricular muscle action potential in a non-invasive manner without performing a catheter examination.

The present invention can calculate an action potential waveform corresponding to each area of a heart and obtain information on an abnormal ventricular muscle action potential in a non-invasive manner.

What is claimed is:

1. A biomagnetic measurement apparatus comprising means for detecting a magnetic field produced from a heart, means for calculating current vectors from said detected magnetic field, and for calculating a potential waveform corresponding to a ventricular muscle cell action potential based on the change of absolute values of said current vectors with time, and means for displaying said potential waveform;

wherein said potential waveform is calculated by adding the absolute values of said current vectors in a period from a start time of depolarization of the heart to an end time of depolarization of the heart, and said potential waveform is calculated by subtracting the absolute values of said current vectors from the value of said potential waveform at the end of depolarization of the heart in a period from the end of depolarization of the heart to an end time of repolarization of the heart.

2. The biomagnetic measurement apparatus according to claim 1, wherein said magnetic fields are detected at a plurality of different measurement points, said current vectors are calculated at said plurality of measurement points, and said potential waveforms obtained based on the change of the absolute values of said current vectors with time are displayed.

3. The biomagnetic measurement apparatus according to claim 1, wherein said means displaying a potential waveform displays the waveform of said measured magnetic field and said potential waveform at the same time.

4. A biomagnetic measurement apparatus comprising a plurality of detection coils detecting, when a plane in parallel with a plane contacted with a living body is xy plane and an axis vertical to said (x, y) plane is z, element Bz in z direction of a magnetic field produced from said living body at a plurality of measurement points (x, y), a data collection device collecting detected signal data of the element Bz in said z direction, an operation processor performing operation processing of said collected signal data, and a display device displaying the result of said operation processing, wherein said operation processor executes first operation processing in which when $t=t_i$ ($i=0, 1, \ldots, m$) is a period corresponding to depolarization of the heart of said living body and $t=t_i$ ($i=m+1, m+2, \ldots, n$) is a period corresponding to repolarization of the heart of said living body, from the element Bz in said z direction at time $t=t_i$ ($i=0, 1, \ldots, n$) at said measurement point (x, y), a current vector (Ix (t), Iy (t)) and an absolute value of said current vector $Ixy(t)=\sqrt{\{(Ix(t))^2+(Iy(t))^2\}}$ are calculated, second operation processing in which when the lower limit of addition $\Sigma$ is $i=0$ and the upper limit of addition $\Sigma$ is $i=0, 1, \ldots, m$, a potential waveform in a period corresponding to depolarization of the heart of said living body is calculated by using $V(t_i)=\Sigma Ixy(t_i)$, and third operation processing in which when the value of said potential waveform $V(t_m)$ at the end of a period corresponding to depolarization of the heart of said living body is $V_m$, the lower limit of addition $\Sigma$ is $i=m+1$ and the upper limit of addition $\Sigma$ is $i=m+1, m+2, \ldots, n$, a potential waveform in a period corresponding to repolarization of the heart of said living body is calculated by using $V(t_i)=V_m-\Sigma Ixy(t_i)$, and said display device displays said potential waveform corresponding to said measurement point (x, y) obtained by said second and said third operation processing.

5. The biomagnetic measurement apparatus according to claim 4, wherein said potential waveforms V are calculated at said plurality of measurement points.

6. The biomagnetic measurement apparatus according to claim 5, wherein said display device displays the waveforms of said measured magnetic fields and said potential waveforms V.

7. The biomagnetic measurement apparatus according to claim 5, wherein said display device performs contour map display of said potential waveforms V.

8. A biomagnetic measurement apparatus, comprising calculating means wherein when a plane in parallel with a plane contacted with the surface of a chest is xy plane and an axis vertical to said x, y plane is z, magnetic fields produced from a heart are detected at a plurality of measurement points (x, y) to calculate current vectors from said detected magnetic fields, wherein when start time of depolarization of the heart is $t_0$, end time of depolarization of the heart is $t_m$, end time of repolarization of the heart is $t_n$, an absolute value of said current vector at time $t_i$ is $Ixy(t_i)$ ($i=1,2,\ldots,n$), and a potential waveform at said time $t_0$ is $V(t_0)=0$, a potential waveform at time $t_i$ in a period from said time $t_0$ to said time $t_m$ is calculated by using $V(t_i)=V(t_{i-1})+Ixy(t_i)$, the value of potential waveform $V(t_m)$ at said time $t_m$ is $V_m$, a potential waveform at said time $t_{m+1}$ is calculated by using $V(t_{m+1})=V_m-Ixy(t_{m+1})$, a potential waveform at time $t_i$ in a period from time $t_{m+2}$ to time $t_n$ is calculated by using $V(t_i)=V(t_{i-1})Ixy(t_i)$, and said potential waveform $V(t_i)$ is calculated at said measurement point (x, y), and means for displaying said potential waveform.

9. The biomagnetic measurement apparatus according to claim 8, wherein said potential waveforms corresponding to said plurality of measurement points (x, y) are displayed at the same time.

10. A bioniagnetic measurement apparatus, comprising calculating means wherein when a plane in parallel with a plane contacted with the surface of a chest is an xy plane and an axis vertical to said xy plane is z, magnetic fields produced from a heart are detected at a plurality of measurement points (x, y) to calculate current vectors, wherein in a period from a start time of depolarization of the heart to an end time of depolarization of the heart, absolute values of said current vectors are added to calculate a potential waveform, and in a period from the end of depolarization of the heart to an end time of repolarization of the heart, the absolute values of said current vectors are subtracted from the value of said potential waveform at the end of depolarization of the heart to calculate said potential waveform at said measurement point (x, y) and means for displaying said potential waveform.

11. A biomagnetic measurement apparatus which detects a magnetic field produced from a heart to calculate current vectors, comprising a display device displaying a potential waveform corresponding to a ventricular muscle cell action potential obtained based on the change of the absolute values of said current vectors with time and, calculating means wherein in a period from start time of depolarization of the heart to an end time of depolarization of the heart, said potential waveform is calculated by adding absolute values of said current vectors; and in a period from the end of depolarization of the heart to an end time of repolarization of the heart, said potential waveform is calculated by subtracting the absolute values of said current vectors from the value of said potential waveform at the end of depolarization of the heart.

12. The biomagnetic measurement apparatus according to claim 11, wherein said magnetic fields are detected at a plurality of measurement points, said current vectors are calculated at said plurality of measurement points, and said potential waveforms obtained based on the change of the absolute values of said current vectors with time are displayed on said display device.

13. The biomagnetic measurement apparatus according to claim 11, wherein said display device displays the potential waveform of said measured magnetic field and said potential waveform at the same time.

* * * * *